United States Patent
Weiss et al.

(10) Patent No.: US 9,222,883 B2
(45) Date of Patent: Dec. 29, 2015

(54) OPTICAL MEASURING SYSTEM HAVING A CELL HOLDER TO ACCOMMODATE FLOW THROUGH CELLS OF DIFFERENT DIMENSIONS IN THE DIRECTION OF OPTICAL PATH

(75) Inventors: Michael Weiss, Gerlingen (DE); Guido Mertens, Boblingen (DE)

(73) Assignee: Endress + Hauser Conducta Gesellschaft für Mess—und Regeltechnik mbH + Co. KG, Dieselstr, Gerlingen (DE)

( * ) Notice: Subject to any disclaimer, the term of this patent is extended or adjusted under 35 U.S.C. 154(b) by 403 days.

(21) Appl. No.: 13/812,019

(22) PCT Filed: Jul. 25, 2011

(86) PCT No.: PCT/EP2011/062749
§ 371 (c)(1),
(2), (4) Date: Apr. 1, 2013

(87) PCT Pub. No.: WO2012/013635
PCT Pub. Date: Feb. 2, 2012

(65) Prior Publication Data
US 2013/0187067 A1    Jul. 25, 2013

(30) Foreign Application Priority Data
Jul. 26, 2010  (DE) .......... 10 2010 038 428

(51) Int. Cl.
*G01N 15/06*  (2006.01)
*G01N 21/59*  (2006.01)
(Continued)

(52) U.S. Cl.
CPC .............. *G01N 21/59* (2013.01); *G01N 21/05* (2013.01); *A61L 2/081* (2013.01); *G01N 2021/0367* (2013.01)

(58) Field of Classification Search
CPC .................. B01L 3/502715; B01L 2200/027; B01L 2300/0877; B01L 2300/0829; G01N 21/05; G01N 2001/2057; G01N 2021/0321; G01N 21/59

USPC ........... 250/573, 575, 576, 239; 356/318, 72, 356/73, 417
See application file for complete search history.

(56) References Cited

U.S. PATENT DOCUMENTS 2,999,417 A    12/1961   Isreeli
3,046,831 A     7/1962   Isreeli
(Continued)

FOREIGN PATENT DOCUMENTS

CN      101611305 A    12/2009
DE        1119545 B    12/1961
(Continued)

OTHER PUBLICATIONS

German Search Report dated Feb. 9, 2011, issued in Application No. 10 2010 038 428.3, in Munich, Germany.
(Continued)

*Primary Examiner* — Que T Le
(74) *Attorney, Agent, or Firm* — Bacon & Thomas, PLLC

(57) ABSTRACT

An optical measuring system includes at least one radiation source, at least one radiation receiver, and at least one flow through cell. The radiation emitted by the at least one radiation source passes at least partially in an optical path between the radiation source and the radiation receiver through the flow through cell and then strikes the at least one radiation receiver. The radiation receiver is embodied to output a signal dependent on the intensity of the radiation striking the radiation receiver, wherein the flow through cell is arranged in a cell holder, which is connected via a first connection interface releasably with the radiation receiver and which is connected via a second connection interface releasably with the radiation source.

9 Claims, 3 Drawing Sheets

(51) Int. Cl.
   *G01N 21/05* (2006.01)
   *A61L 2/08* (2006.01)
   *G01N 21/03* (2006.01)

(56) References Cited

U.S. PATENT DOCUMENTS

| | | | |
|---|---|---|---|
| 3,503,683 A * | 3/1970 | Heimann et al. | 356/36 |
| 3,917,404 A | 11/1975 | Heiss | |
| 5,491,344 A * | 2/1996 | Kenny et al. | 250/461.1 |
| 6,069,687 A | 5/2000 | Briggs | |
| 8,268,248 B2 | 9/2012 | Steuerwald et al. | |
| 2012/0119101 A1* | 5/2012 | Wynn | 250/373 |
| 2013/0240747 A1 | 9/2013 | Ehring | |

FOREIGN PATENT DOCUMENTS

| | | | |
|---|---|---|---|
| DE | 25 17 786 A1 | 12/1975 | |
| DE | 102 22 822 A1 | 12/2003 | |
| WO | 94/27495 A1 | 12/1994 | |
| WO | 03/098198 A1 | 11/2003 | |
| WO | 2004/090513 A1 | 10/2004 | |
| WO | 2010/081790 A1 | 7/2010 | |

OTHER PUBLICATIONS

International Preliminary Report on Patentability dated Oct. 13, 2011, issued in Application No. PCT/EP2011/062749, in Rijswijk, Netherlands.

International Preliminary Report on Patentability dated Feb. 7, 2013, issued in Application No. PCT/EP2011/062749, in Geneva, Switzerland.

* cited by examiner

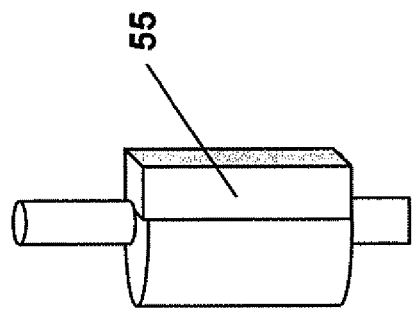
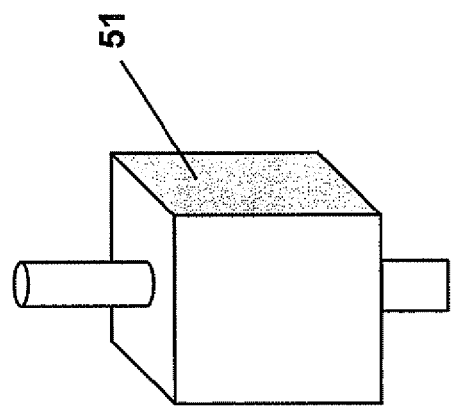
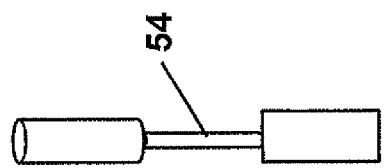
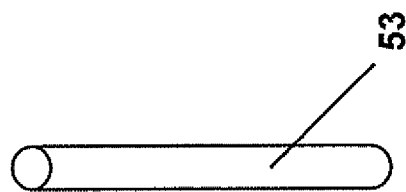
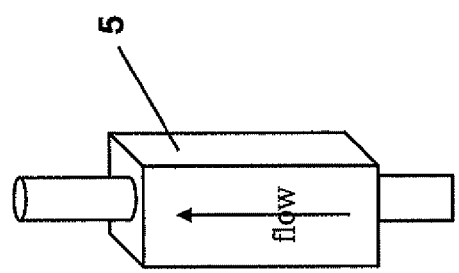
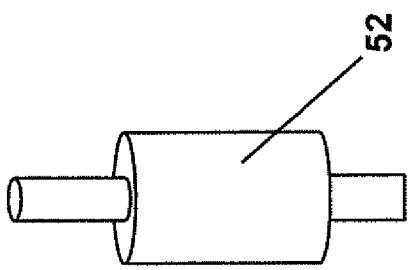
Fig. 3

OPTICAL MEASURING SYSTEM HAVING A CELL HOLDER TO ACCOMMODATE FLOW THROUGH CELLS OF DIFFERENT DIMENSIONS IN THE DIRECTION OF OPTICAL PATH

TECHNICAL FIELD

The invention relates to an optical measuring system, which includes at least one radiation source, at least one radiation receiver and at least one flow through cell, wherein radiation emitted by the at least one radiation source passes at least partially in an optical path between the radiation source and the radiation receiver through the flow through cell and then strikes the at least one radiation receiver, and wherein the radiation receiver is embodied to output a signal dependent on the intensity of the radiation striking the radiation receiver.

BACKGROUND DISCUSSION

Such measuring systems are inserted, for example, in online-analyzers of process measurements technology. Examples are known from WO 2004/090513 A1 or DE 102 22 822 A1.

In the case of such measuring systems, radiation emitted by the radiation source, in given cases, as a beam or a reference beam formed with the assistance of optical elements, such as e.g. lenses, mirrors, beam dividers or optical fibers, is sent at least partially on the optical path through the flow through cell. In such case, there occurs an interaction between the radiation and the measured medium contained in the flow through cell. The interaction can lead especially to an absorption of at least part of the radiation, e.g. in a certain wavelength range. After passing through the flow through cell, the radiation changed by the interaction strikes the radiation receiver, which outputs a measurement signal dependent on the intensity of the striking radiation. From the measurement signal, deductions can be made concerning the interaction with the measured medium and, therewith, concerning the nature and/or composition of the measured medium, especially the concentration of an analyte in the measured medium.

The radiation can be led from the radiation source to the flow through cell and from the flow through cell to the radiation receiver by means of optical fibers.

For applications of such optical measuring systems in industrial biological, biochemical or biotechnological processes, it can be required that a sterile flow through cell be used. In biological, biochemical or biotechnological processes, the sterilizing of components, which are to come in contact with the process medium, especially with bacteria or yeasts used for biotechnological production, is frequently performed by irradiating with intensive gamma radiation. The gamma radiation can, however, lead to the damaging of other components of the measuring system, especially the radiation receiver or electronics arranged near the flow through cell. Unconditionally to be prevented, moreover, in biochemical, biological or biotechnological processes is cross contamination, which can occur, when a flow through cell is reused for measurements in different stages of a process or for measurements on different systems, i.e. different measured media.

SUMMARY OF THE INVENTION

It is therefore an object of the invention to provide an optical measuring system, which takes into consideration the said requirements in biological, biotechnological or biochemical applications, especially in process measurements technology. Especially, the flow through cell should be easily sterilizable, without subjecting other components of the measuring system to danger of damage. Furthermore, ideally without complex cleaning steps between individual measurements, different measured media should be able to be examined in measurements following one after another.

The object is achieved by an optical measuring system comprising at least one radiation source, at least one radiation receiver, and at least one flow through cell, wherein radiation emitted by the at least one radiation source passes at least partially as measuring radiation on an optical path through the flow through cell and then strikes the at least one radiation receiver, and wherein the radiation receiver is embodied to output a signal dependent on an intensity of the radiation striking the radiation receiver, wherein the flow through cell is arranged in a cell holder, which is connected via a first connection interface releasably with the radiation receiver and which is connected via a second connection interface releasably with the radiation source.

Since the flow through cell is arranged in a cell holder, which is connected respectively via connection interfaces with the radiation source and with the radiation receiver, it is possible to replace the flow through cell in simple manner. Especially, the cell holder including the flow through cell can be removed from the measuring system and the flow through cell can be replaced between two measurements. The flow through cell can be sterilized with gamma radiation outside of the measuring system either already in the cell housing or yet before being affixed in the cell housing. Due to the so established replaceability of the flow through cell, or the flow through cell with cell holder, a modular measuring system can be implemented, wherein the cell holder is so embodied that flow through cells of different material, which, for example, is transmissive for radiation of different wavelength ranges, and flow through cells with different dimensions in the direction of the optical path, can be inserted into the cell holder as a function of desired application. In this way, correspondingly suitable flow through cells can be provided for measurements following one after the other with the measuring system, depending on desired measuring wavelength or depending on the desired optical path length of the measuring radiation through the measured medium contained in the flow through cell.

After the replacement of a used flow through cell, the used cell can be disposed of. Since the used flow through cells are disposed of and not recleaned and inserted back for other measurements, cross contamination is prevented.

The cell holder can be embodied, for example, as a closed cell housing, in which the flow through cell is mounted in a fixed position, and which has an opening, or window, for the entering and exiting of the measuring radiation into the cell housing, respectively from the cell housing.

The radiation source can comprise one or more UV light emitting diodes (UV-LEDs). They can supplementally or alternatively comprise one or more light emitting diodes, which emit radiation of one or more wavelengths of the wavelength region between 100 and 2500 nm. Preferably, the light emitting diodes emit the radiation source radiation in the UV/Vis range. The radiation source can also be a broadband radiation source, for example, a flash lamp or a xenon lamp. In this case, the radiation source can comprise one or more filters, especially an adaptable filter, for selecting a desired measuring wavelength.

The radiation receiver can comprise a photodiode, a photodiode array, a CCD camera or some other suitable optoelectronic apparatus.

In an embodiment, the radiation receiver can be arranged in a receiver housing, which is connected releasably with the first connection interface of the cell holder, especially the cell housing, wherein the first connection interface has mechanical securement means, which engage in thereto complementary securement means of the receiver housing, in order to fix the cell holder and the therein arranged, flow through cell in a predetermined orientation relative to the receiver housing, and wherein the first connection interface has an opening surrounding the optical path or a window arranged within the optical path, and at least partially transparent for the radiation emitted by the radiation source.

The first connection interface can comprise as mechanical securement means especially a screw thread, a bayonet connection or a mechanical connector with one or more flexible detents, which can engage with a thereto complementary screw thread, bayonet connection counterpart or a protrusion or groove of the receiver housing embodied for receiving the flexible detent(s).

In an additional embodiment, the radiation source can be arranged in a source housing, which is connected releasably with the second connection interface of the cell holder, especially the cell housing, wherein the second connection interface has mechanical securement means, which engage in thereto complementary securement means of the source housing, in order to affix the cell holder and the therein arranged flow through cell in a predetermined orientation relative to the source housing, and wherein the second connection interface has an opening surrounding the optical path or a window arranged within the optical path and at least partially transparent to the radiation emitted by the radiation source.

As earlier described for the first connection interface, also the second connection interface can comprise as mechanical securement means especially a screw thread, a bayonet connection or a mechanical connector with one or more flexible detents, which can be brought into engagement with a thereto complementary screw thread, bayonet connection-counterpart or a protrusion or groove of the receiver housing embodied for accommodating the flexible detent(s).

The flow through cell can have an inlet and an outlet for a measured medium, especially a measured liquid. When the cell holder is embodied as a cell housing surrounding the flow through cell, the inlet and the outlet can be connected with, in each case, a media line, especially a hose, wherein the inlet or the media line connected with the inlet is led through a first wall of the cell housing, and wherein the outlet or the media line connected with the outlet is led through a second wall of the cell housing, especially a wall different from the first wall, of the cell housing in which the flow through cell is arranged, and be connected, in each case, with a media line, especially a hose. The inlet and outlet can be embodied as tubular projections of the flow through cell or also only as openings or connections of the flow through cell, to which the lines for medium are connectable.

The lines for medium can be connected to a process to be monitored, for example, a chromatographic column of a biotechnological cleanup process (a downstream process). For this, the lines for medium can be connected sealedly and sterilely via conventional connectors for sealed and sterile connection to biotech processes.

During replacement of the flow through cell, the lines for medium can also be replaced. In this case, the lines for medium are separated from the connectors, wherein, after separation, the process to be monitored can remain sealed relative to the environment. Preferably, the lines for medium and/or the inlet, or outlet, of the flow measuring cell are likewise sterilely sealable relative to the environment by means of valves.

The cell holder can be embodied to accommodate flow through cells of different dimensions in the direction of the optical path. In this way, various optical path lengths can be provided through the measured medium. Depending on application, a flow through cell of the desired path length through the measured medium can be provided.

The flow through cell can be formed of one of the materials, quartz, quartz glass, sapphire and MMApolymethylmethacrylate). Preferably, different measuring cells of equal or different dimensions and different materials can be held in inventory. Depending on desired wavelengths of the measuring radiation emitted by the radiation source, then a suitable material, i.e. a material transparent for the measuring wavelength, can be selected.

Alternatively, the flow through cell can be formed also partially of a material non-transmissive for the measuring radiation, and only in the region of the optical path have windows of one of the materials, quartz, quartz glass, sapphire and PMMA.

A method for operating an optical measuring system according to one of the above embodiments for performing a series of measurements, especially measurements following one after another in time, includes the following steps:
 for performing a first measurement, affixing a first flow through cell in the cell holder, and, especially thereafter, connecting the cell holder via the first connection interface with the receiver housing as well as via the second connection interface with the source housing;
 performing the first measurement;
 for performing a second measurement, removing the first flow through cell from the cell holder and affixing a second flow through cell in the cell holder, and, especially thereafter, connecting the cell holder via the first connection interface with the receiver housing as well as via the second connection interface with the source housing; and
 performing the second measurement;
 wherein the performing of a measurement includes irradiating the flow through cell with radiation emitted by the radiation source along the optical path and registering a measurement signal produced by the radiation striking the radiation receiver after passing through the optical path.

The first and second measurements can directly follow one another. It is, however, also an option that between the first measurement with the first flow through cell and the second measurement with the second flow through cell a series of additional measurements with the first flow through cell is performed, and then the first flow through cell is replaced with the second flow through cell.

Preferably, for affixing the first and second flow through cells in the cell holder, the connections of the cell holder with the receiver housing and the source housing are released and the cell holder removed from the measuring system. The first flow through cell taken from the cell holder after the first measurement can immediately be disposed of. Since the flow through cells are disposed of and not recleaned and placed back for further measurements, the cross contamination mentioned above is prevented.

The first flow through cell can be of another material than the second flow through cell. Alternatively or supplementally, the first flow through cell and the second flow through cell can have different dimensions in the direction of the optical path.

In this way, an option is to perform sequential measurements with different path lengths through the measured medium and/or with different wavelengths.

Preferably, the first and second flow through cells are sterilized by means of gamma radiation before connecting the cell holder with the receiver housing and the source housing. As already explained above in connection with the optical measuring system, the sterilizing can be performed in the case of the flow through cell already affixed in the holder or even before the flow through cell is mounted in the cell holder. The sterilized flow through cell is sealed sterilely relative to the environment by means of valves arranged in the inlet and outlet of the flow through cell or by means of films completely sealing the inlet and outlet of the flow through cell or by means of some other suitable closure. After connecting the flow through cell to the lines for medium, the films or the closures are removed or the valves opened.

When the newly to be installed flow through cell as above described is inserted into the measuring system simultaneously with the connected lines for medium, the flow through cell and the lines for medium can be simultaneously sterilized. Correspondingly, the sterilized lines for medium are sealed sterilely relative to the environment by means of valves, or the ends of the lines for medium not connected with the flow through cell are sealed sterilely relative to the environment by means of films or other suitable closures completely sealing the lines for medium. After connecting the lines for medium to the process to be monitored, the films or the closures are removed or the valves opened. Suitable connectors, which seal the sterile lines for medium in suitable manner before the connecting to the process are known to those skilled in the art. Thus e.g. Pall connectors can be used.

For replacement of the receiver or the light source, the receiver housing and/or the source housing of the arrangement can be removed, and a new receiver housing and/or a new source housing placed back into the arrangement. Through the interfaces between the cell holder and the receiver housing, or between the cell holder and the source housing, a certain separation between the light source and the receiver is fixedly predetermined, so that, before start-up of the measuring system after replacement of the light source and/or the receiver, no renewed adjusting is required.

BRIEF DESCRIPTION OF THE DRAWINGS

The invention will now be explained in detail based on the examples of embodiments shown in the drawing, the figures of which show as follows:

FIG. 3 are schematic representations of flow through cells of different geometries.

DETAILED DISCUSSION IN CONJUNCTION WITH THE DRAWINGS

Figure 1:
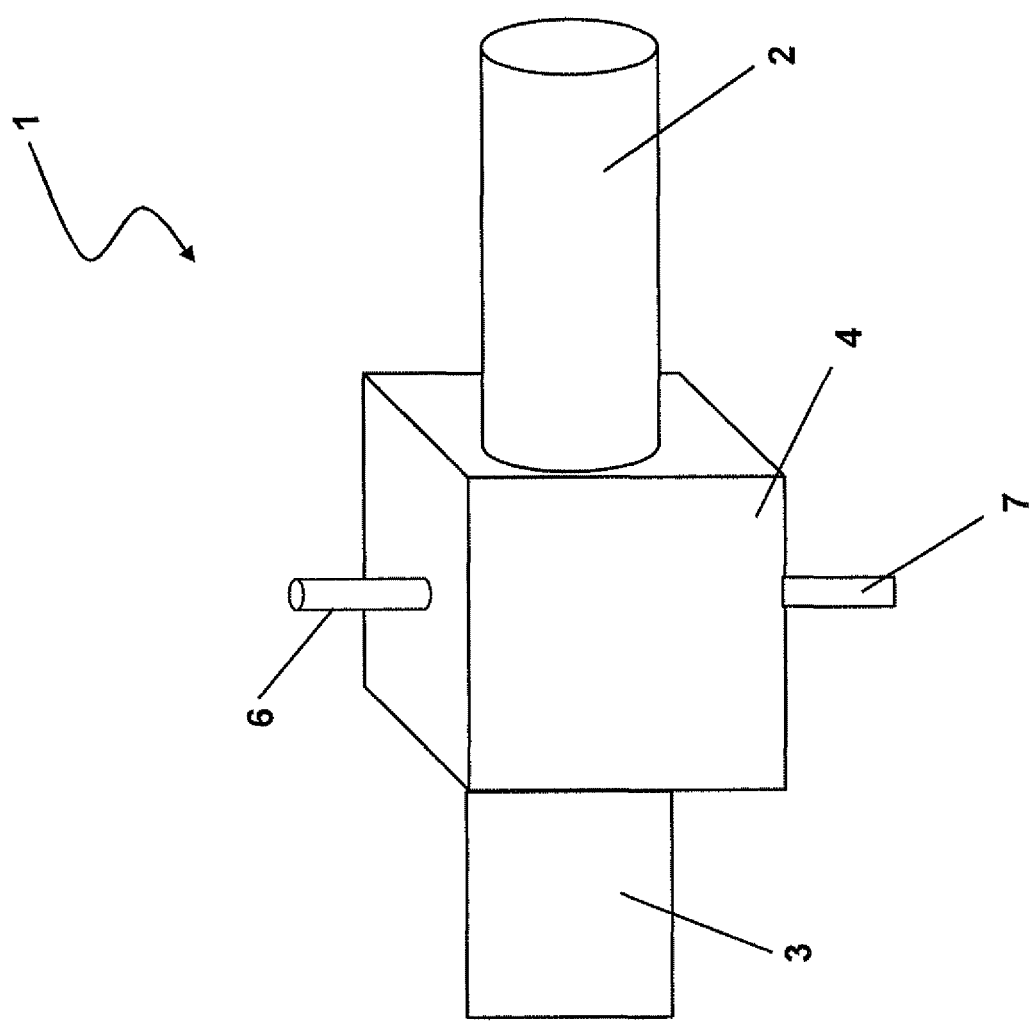
FIG. 1 is a schematic representation of a measuring system with a radiation source, a cell holder and a radiation receiver.

FIG. 1 shows an optical measuring system 1 having a source housing 2, in which a radiation source is arranged, a receiver housing 3, in which a radiation receiver is arranged, and a cell holder 4 arranged between the source housing 2 and the receiver housing 3 and embodied as a cell housing. Cell holder 4 contains, as will be explained in greater detail based on FIG. 2, a flow through cell 5, of which there appears in FIG. 1 only the measured medium inlet 6 led through an upper housing wall of the cell holder 4 and the measured medium outlet 7 led through a lower housing wall of the cell holder 4.

The radiation source can be a monochromatic radiation source, e.g. a diode emitting light of a predetermined wavelength, a number of monochromatic radiation sources, e.g. a number of light emitting diodes having predetermined emission wavelengths, or a polychromatic radiation source, for example, a flash lamp. The radiation emitted by the radiation source is in the form of a measuring beam. Thus, the measuring beam is formed, in given cases, by means of one or more optical elements, e.g. lenses, mirrors, orifices, beam dividers. The measuring beam extends along an optical path, also called the measuring path, between the radiation source and the radiation receiver and through the flow through cell. The radiation receiver can comprise one or more photodiodes or a CCD camera. The radiation receiver outputs an electrical measurement signal dependent on the intensity of the radiation striking it, especially the radiation of the measuring beam. The measurement signal is processed by an evaluating unit (not shown) of the optical measuring system 1 to form a measured value, which is then output. The measured value can be, for example, a concentration of an analyte, however, also an absorption value, or a radiation intensity or a spectrum.

Cell holder 4 is connected releasably with the source housing and the receiver housing 3. Through the connection, the flow through cell 5 affixed in the cell holder 4 is arranged in a fixed position and orientation relative to the radiation source arranged in the source housing 2 and the radiation receiver accommodated in the receiver housing 3, so that, in the case of replacement of the flow through cell 5 with another flow through cell of equal geometry and especially the same dimensions, there remains along the optical path an equal separation between the radiation source, the flow through cell 5 and the radiation receiver. In this way, on the one hand, a reproducible measurement signal of the radiation receiver is assured. On the other hand, an adapting of the distances or a focusing of the measuring beam extending along the optical path from the radiation source through the flow through cell 5 to the radiation receiver is not required.

Figure 2:
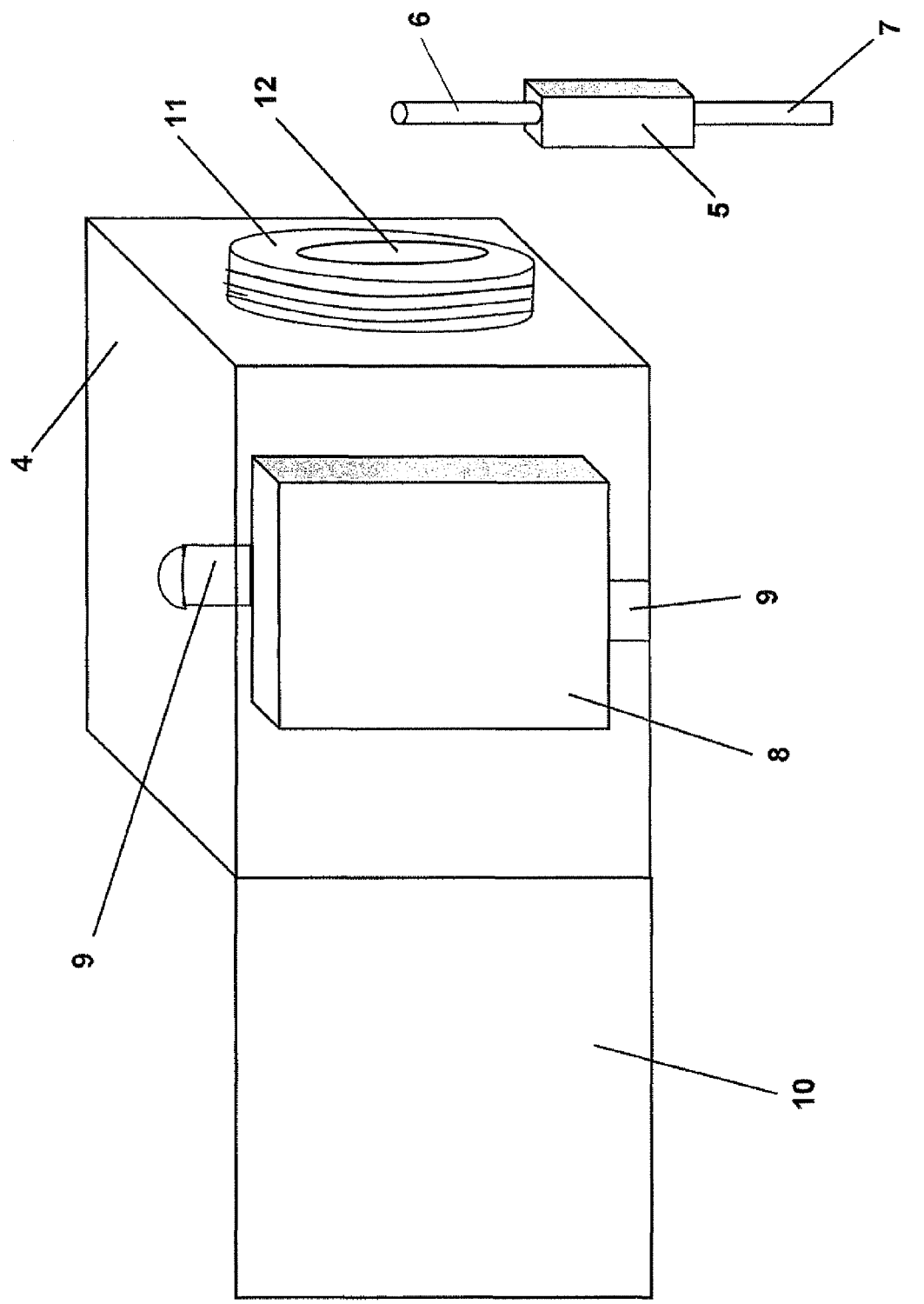
FIG. 2 is a schematic representation of a cell holder embodied as cell housing.

FIG. 2 shows the cell holder 4 in detail. In the example shown here, it is embodied as a cell housing closed to the environment. The cell housing includes a recess 8, into which the flow through cell 5 is insertable. The inlet 6 and the outlet 7 of the flow through cell 5 can be accommodated in the bores 9 of the cell housing and so be led through two oppositely lying walls of the cell housing. Alternatively, the bores 9 can also accommodate lines for medium, for example, hoses, which can be connected directly to the flow through cell 5.

One of the walls of the cell housing is embodied as a movable door 10, which can be opened for inserting, or removing, the flow through cell 5. Following insertion of the flow through cell 5, the door 10 is closed and seals the cell housing from the environment. Cell holder 4 is releasably connectable with the source housing 2, or the detector housing 3, by means of a connection interface 11, which in the present example is embodied as a connector with a screw thread. In the example shown here, cell holder 4 has two identically embodied connection interfaces 11 on oppositely lying sides, so that on one side a releasable connection with the source housing 2 is formed and on the oppositely lying side a releasable connection with the detector housing 3 is formed (FIG. 1).

The connection interfaces 11 each have an opening 12, through which extends the optical path between the radiation source arranged in the source housing 2 and the radiation receiver arranged in the detector housing 3. The openings 12 of the oppositely lying connection interfaces align with one another and with the flow through cell 5, so that radiation emitted by the radiation source passes through the flow through cell 5 and strikes the radiation receiver after exiting from the flow through cell 5.

FIG. 3 shows different flow through cells. In order to provide different optical path lengths, different flow through cells can be inserted into the cell holder. Cell holder 4 of the optical measuring system 1 can preferably be so embodied, that all illustrated flow through cells 5, 51 52, 53, 54 and 55 can be accommodated in the cell holder 4. Alternatively, the cell holder can also only be suitable for accommodating some or individual ones of the illustrated flow through cells 5, 51, 52, 53, 54 or 55. In the example illustrated in FIG. 2, the flow through cells 5, 51, 53, 54 and 55 can be inserted into the recess 8. If, in sequential measurements, different optical path lengths are to be made available for the measuring radiation traveling through the flow through cell, then, for example, in a first measurement, the flow through cell 5 can be inserted. Later, flow through cell 5 can be replaced by the flow through cell 51, in order to have for a second measurement a longer optical path length through the measured medium. This can be desirable, for example, when absorption or turbidity of the measured medium changes as a function of time, so that, for example, first of all, a medium with high turbidity or absorption flows through the flow through cell, while later a medium with low turbidity or absorption flows through the flow through cell.

The different geometries of the flow through cells permit matching the dispersion of the measuring radiation traveling through the flow through cells. The curved walls of the flow through cells 52, 53 and 54 act as optical elements for beam forming.

The flow through cells illustrated in FIG. 3 can be composed of different materials. Also flow through cells of all shown geometries can be provided manufactured of different materials. In this way, depending on application, a flow through cell of suitable geometry, especially with a suitable dimension in the direction of the optical path for providing a suitable optical path length for the measuring radiation, and of a suitable material, which is, on the one hand, chemically inert relative to the measured medium and which, on the other hand, is transparent for the wavelength of the measuring radiation, can be inserted.

Suitable materials can be, for example, synthetic material, e.g. plastic, especially PMMA (polymethylmethacrylate), quartz, or quartz glass or sapphire.

The invention claimed is:

1. An optical measuring system, comprising:
at least one radiation source;
at least one radiation receiver; and
at least one flow through cell, wherein:
radiation emitted by said at least one radiation source passes at least partially on in optical path between said at least one radiation source and said at least one radiation receiver through said at least one flow through cell and then strikes said at least one radiation receiver;
said at least one radiation receiver is embodied to output a signal dependent on the intensity of the radiation striking said at least one radiation receiver; and
said at least one flow through cell is arranged in a cell holder, which is connected via a first connection interface releasably with said at least one radiation receiver and which is connected via a second connection interface releasably with said at least one radiation source; and
said cell holder is embodied to accommodate flow through cells of different dimensions in the direction of the optical path.

2. The optical measuring system as claimed in claim 1, wherein:
said at least one radiation receiver is arranged in a receiver housing, which is connected releasably with said first connection interface of said cell holder;
said first connection interface has mechanical securement means, which engage in thereto complementary securement means of said receiver housing, in order to fix said cell holder and the therein arranged, at least one flow through cell in a predetermined orientation relative to said receiver housing; and
said first connection interface has an opening surrounding the optical path or a window arranged in the optical path.

3. The optical measuring system as claimed in claim 1, wherein:
said at least one radiation source is arranged in a source housing, which is releasably connected with said second connection interface of said cell holder;
said second connection interface has mechanical securement means, which engage in thereto complementary securement means of said source housing, in order to affix said cell holder and the therein arranged said at least one flow through cell in a predetermined orientation relative to said source housing; and
said second connection interface has an opening surrounding the optical path or a window arranged in the optical path.

4. The optical measuring system as claimed in claim 1, wherein:
said cell holder is a cell housing surrounding said at least one flow through cell; and
said at least one flow through cell has an inlet and an outlet for a measured medium, especially a measured liquid;
said inlet and said outlet are connected with, in each case, a media line, especially a hose;
said inlet or the media line connected with the inlet is led through a first wall of said cell housing; and
said outlet or the media line connected with the outlet is led through a second wall of said cell housing, especially a second wall different from said first wall, of the cell housing in which said at least one flow through cell is arranged, and are connected, in each case, with a media line, especially a hose.

5. The optical measuring system as claimed in claim 1, wherein:
said at least one flow through cell is formed of one of the materials: quartz, quartz glass, sapphire and PMMA.

6. The optical measuring system as claimed in claim 1, wherein:
said at least one flow through cell comprises at least one window, which is formed of one of the materials: quartz, quartz glass, sapphire and PMMA.

7. A method for operating an optical measuring system, said measuring system comprising: at least one radiation source; at least one radiation receiver; and at least one flow through cell, wherein: radiation emitted by said at least one radiation source passes at least partially on an optical path between said at least one radiation source and said at least one radiation receiver through said at least one flow through cell and then strikes said at least one radiation receiver; said at least one radiation receiver is embodied to output a signal dependent on the intensity of the radiation striking said at least one radiation receiver; and said at least one flow through cell is arranged in a cell holder, which is connected via a first connection interface releasably with said at least one radiation receiver and which is connected via a second connection interface releasably with said at least one radiation source;
said method comprising:
performing a series of measurements, wherein a measurement includes irradiating the flow through cell with radiation emitted by the radiation source along the optical path and registering a measurement signal produced by the radiation striking the radiation receiver after passing through the optical path, comprising affixing a first flow through cell in the cell holder, and connecting the cell holder via the first connection interface with the radiation receiver as well as via the second connection interface with the radiation source;

performing the first measurement;

for performing a second measurement, removing the first flow through cell from the cell holder and affixing a second flow through cell in the cell holder, and connecting the cell holder via the first connection interface with the radiation receiver as well as via the second connection interface with the radiation source; and performing the second measurement;

said first flow through cell and the second flow through cell having different dimensions in the direction of the optical path.

8. The method as claimed in claim 7, wherein:

the first flow through cell is composed of another material than the second flow through cell.

9. The method as claimed in claim 7, wherein:

the first and second flow through cells are sterilized by means of gamma radiation before connecting the cell holder with the receiver housing and the source housing.

\* \* \* \* \*